US005767634A

United States Patent [19]

Taylor et al.

[11] Patent Number: 5,767,634

[45] Date of Patent: Jun. 16, 1998

[54] HEAD MOUNTED PULSE ACTION FACIAL MASSAGER

[75] Inventors: Charles E. Taylor, San Rafael, Calif.; Blaine M. Smith, Lincoln City, Oreg.

[73] Assignee: The Sharper Image, San Francisco, Calif.

[21] Appl. No.: 755,220

[22] Filed: Nov. 22, 1996

Related U.S. Application Data

[62] Division of Ser. No. 339,030, Nov. 14, 1994, Pat. No. 5,611,771.

[51] Int. Cl.[6] .............................. A61H 1/00; A61B 6/14; H02P 5/16

[52] U.S. Cl. ............................ 318/34; 318/114; 318/254; 601/70; 601/71

[58] Field of Search ............................... 318/34–89, 114, 318/129, 132, 138, 245, 254, 599; 128/52, 33, 32, 36, 44; 250/439 P; 601/70, 71, 79, 48

[56] References Cited

U.S. PATENT DOCUMENTS

| | | | |
|---|---|---|---|
| Re. 31,603 | 6/1984 | Christensen | 318/114 |
| 2,227,276 | 12/1940 | Salit | 128/62 |
| 4,052,981 | 10/1977 | Bachmann | 128/36 |
| 4,105,024 | 8/1978 | Raffel | 128/33 |
| 4,129,808 | 12/1978 | Bregeault et al. | 318/254 |
| 4,232,661 | 11/1980 | Christensen | 128/33 |
| 4,286,162 | 8/1981 | Suzuki | 250/439 P |
| 4,286,163 | 8/1981 | Suzuki | 250/439 P |
| 4,286,199 | 8/1981 | Nagakubo et al. | 318/327 |
| 4,458,183 | 7/1984 | Neilson | 318/139 |
| 4,614,999 | 9/1986 | Onodera et al. | 363/28 |
| 4,841,954 | 6/1989 | Kalsi | 128/36 |
| 4,920,466 | 4/1990 | Liu | 362/105 |
| 5,018,511 | 5/1991 | Yokoi | 128/33 |
| 5,075,608 | 12/1991 | Erdman et al. | 318/599 |
| 5,113,852 | 5/1992 | Murtonen | 128/33 |
| 5,115,769 | 5/1992 | Fiorini | 128/32 |
| 5,421,799 | 6/1995 | Rabin et al. | 601/71 |
| 5,635,807 | 6/1997 | Lautzenhiser | 318/625 |

FOREIGN PATENT DOCUMENTS

| | | | |
|---|---|---|---|
| 405192373 | 8/1993 | Japan | 601/46 |

*Primary Examiner*—Paul Ip

*Attorney, Agent, or Firm*—Flehr Hohbach Test Albritton & Herbert LLP

[57] ABSTRACT

A pulse action facial massager apparatus including a headset assembly for mounting to a user's head. A pair of flexible extension fingers extending from opposite sides of the headset assembly each of which is operably coupled to a vibrating device each generating an independent vibrating action. A tip portion of each extension finger is manually movable for selected contact at independent portions of the user's head. Hence, the respective vibrating device transmits the vibrating action thereof along the extension finger to the respective tip portion. Each vibrating device includes a motor that is controlled by an electronic controller mounted on the headset assembly. The controller permits user-variation of the repetition rate and duty cycle of the motors. This permits the user to vary the vibrational patterns produced by the present invention. In an automatic mode, duty cycle is automatically varied by a sawtooth waveform to produce a dynamically changing pattern of massage intensity. The control also includes a timer that after a preset time gradually diminishes the duty cycle and thus the intensity of the vibrations.

12 Claims, 8 Drawing Sheets

HEAD MOUNTED PULSE ACTION FACIAL MASSAGER

This is a division of application Ser. No. 08/339,030 filed 14 Nov. 1994, now U.S. Pat. No. 5,611,771.

FIELD OF THE INVENTION

The present invention relates generally to electronically pulsating massage devices, and more particularly to head mounted pulsating facial massage devices.

BACKGROUND OF THE INVENTION

Pulsating massage devices are commonly used to relieve muscular pain, to relieve stress, and to produce a generally pleasant sensation. Such device is usually applied directly to the area being massaged, for example by holding the device against a user's neck.

Electric massage units include an electric motor, a mechanical element coupled to the motor to communicate motor-produced vibrations to the user, and an electronic circuit that controls the motor. The control circuit permits a user to turn the massager on and off, and perhaps to vary the intensity or strength of the massage.

Prior art control circuits operate the motor at 100% duty cycle, which is to say that when the massage unit is turned on, the motor is always running. Because the duty cycle is fixed, the intensity or strength of the vibrations is fixed. Prior art controller circuits also operate the motor at a single vibrational rate or frequency. Unfortunately, the fixed duty cycle and fixed motor frequency produce an unvarying pattern of vibrations that can become annoying to the user after a short while.

The control circuit for some massagers includes a timer to turn-off the motor after a preset amount of time, for example after the user falls asleep. Unfortunately the sudden cessation of massage action after the preset time can be so abrupt as to awaken the user.

Vibrations produced by the motor are coupled by the mechanism element to a tapered point that focusses the vibrating action on one region of the user's area being massaged. Some massage units provide a wide-area head that contains tapered heads that move up and down to communicate the vibrating action to a large area of the user's skin being massaged.

Further, prior art massage units are generally designed for hand-held use so that the vibrating head or tapered point can be manually manipulated to contact the desired region of application. Because they are hand-held, at least one of the user's hands is precluded from simultaneously performing another task during self-massage. Further, prior art massage units generally preclude simultaneous massage of multiple regions of the user's body. In addition, such massage units are generally inappropriate for application on the user's face, due in part to the size of the massaging head.

It is known in the art to mount a vibrating facial massage unit to an eyeglass frame, proximate the bridge of the user's nose. While this configuration frees the user's hands for other tasks, only those regions of the user's face in direct contact with the eyeglass frames receive direct massage. Hence, this configuration does not provide for selective massage of other areas of the face, and has limited application for facial massage.

In summary, there is a need for a pulse action massage unit that need not be hand-held while massaging a user. Preferably such massage unit should provide massage to different regions of a user's body simultaneously, including different regions of the user's head. Such a massage unit should provide vibrating focal surfaces that can be selectively positioned by a user to massage different regions of the user's head.

Preferably the controller for such a unit should permit a user to vary the intensity and the pattern of the vibrations produced, as well as the repetition rate of the vibrations. Further, the controller should provide a timer mechanism that permits gradual diminishment of the strength of the vibrations. Preferably the entire massage unit should be self-contained and mountable on a user's head.

The present invention provides such a massage unit.

SUMMARY OF THE INVENTION

The present invention provides a self-contained pulse action facial massage unit that is constructed in a headset worn on a user's head. The massage unit includes a pair of vibration-producing motors, each vibrationally-coupled to a flexible extension finger whose vibrating tip may be user-directed to a desired portion of the user's head.

The unit further includes an electronic controller that provides and controls the energizing motor drive voltage pulses to each vibration-producing motor. The controller can cause the preferably DC motors to produce a dynamically changing pattern of massage intensity. The controller includes a pulse rate sawtooth generator that allows user-variation of the repetition rate of the energizing drive pulses to the motors. By adjusting a variable power threshold voltage level, the duty cycle of the motors may be varied, manually or automatically.

In a manual adjust mode, the controller includes a potentiometer that may be user-adjusted to manually vary the power threshold voltage level, and thus the motors' duty cycle, to provide a desired intensity of massage. The controller also includes an auto-power rate sawtooth generator that outputs a slowly changing waveform. In an automatic power adjust mode, this waveform augments the manually-adjusted power threshold voltage to provide a variable power threshold voltage. This automatic mode continuously varies the duty cycle of the motors, producing a gradually changing pattern of massage intensity. If desired, the repetition rate of this slowly varying waveform may be user-varied. Preferably the controller includes a timer that gradually diminishes the duty cycle and thus the intensity of the vibrations to zero, a preset time after power-on to the massage unit.

Other features and advantages of the invention will appear from the following description in which the preferred embodiments have been set forth in detail, in conjunction with the accompanying drawings.

DETAILED DESCRIPTION OF THE PREFERRED EMBODIMENTS

Figure 1:
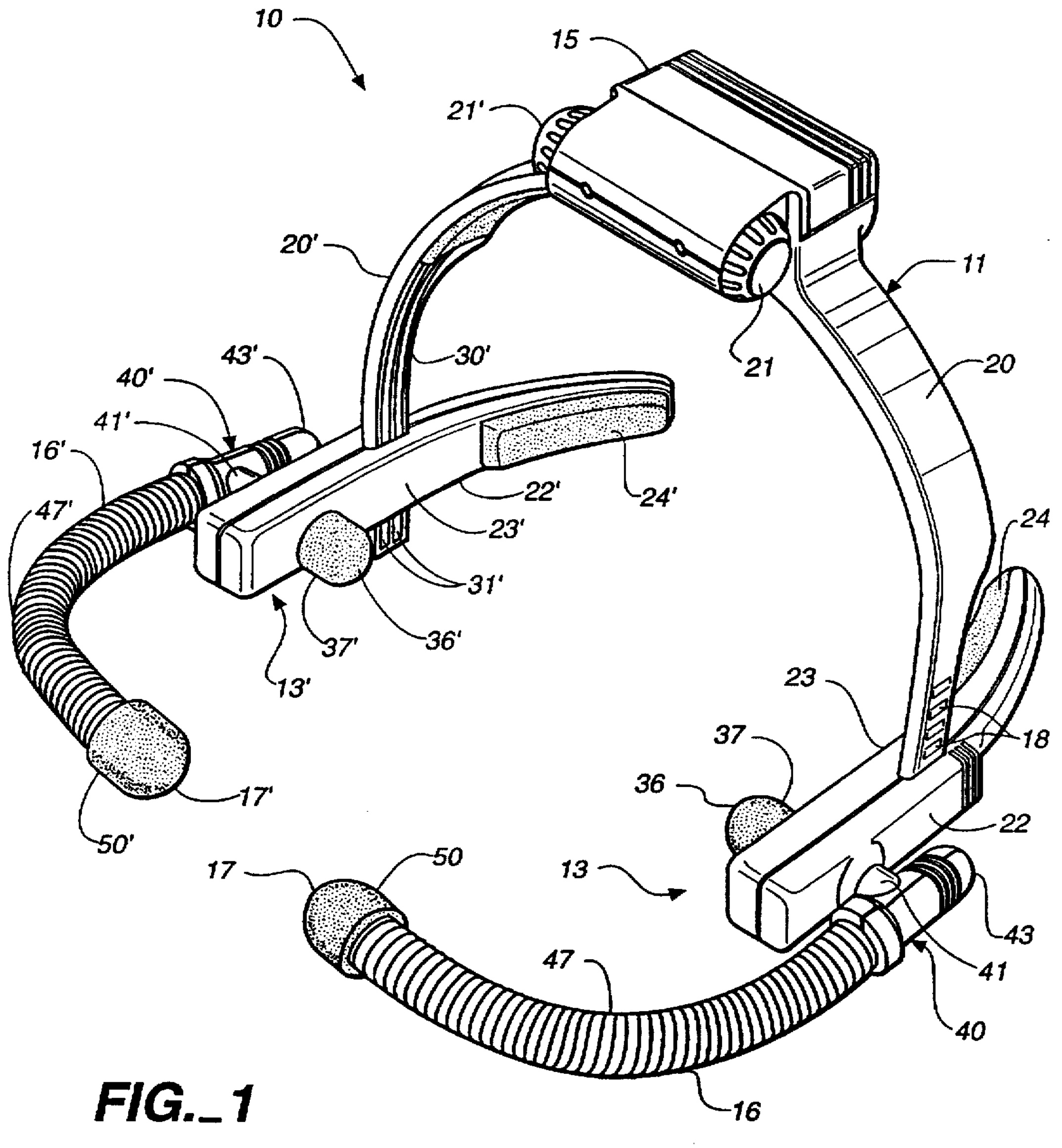
FIG. 1 is a fragmentary, top perspective view of a facial massager apparatus constructed in accordance with the present invention, and mounted to the head of a user shown in phantom lines.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Figure 2:
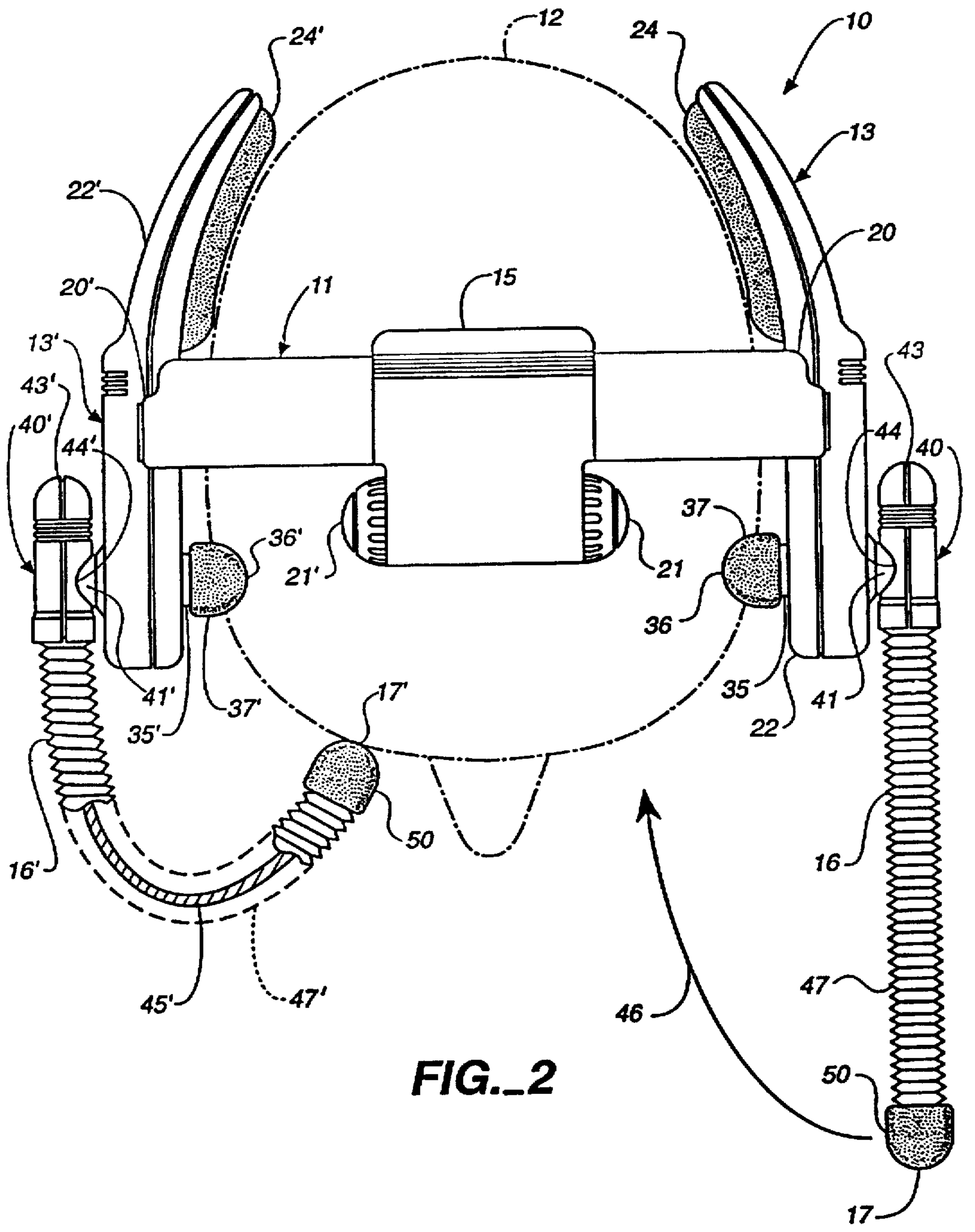
FIG. 2 is a top plan view of the head mounted facial massager apparatus of FIG. 1, and illustrating movement of the extension fingers.

Attention is now directed to FIGS. 1 and 2, where a pulse action facial massager apparatus, generally designated 10, is illustrated including a headset assembly 11 formed and dimensioned for mounting to a user's head 12 (shown phantom lines in FIG. 2). Preferably, a pair of vibration generating assemblies, generally designated 13, 13', are movably mounted to headset assembly 11, each of which includes a motor or vibrating device 14, 14' (FIG. 4) generating an independent vibrating action. A controller device 15 is operably coupled to each vibrating device 14, 14' for independent control of the vibrating action thereof. Each vibration generating assembly 13, 13– of the present invention further includes a pair of flexible extension fingers, generally designated 16, 16–, extending from opposite sides of headset assembly 11. Each extension finger 16, 16' includes a tip portion 17, 17' manually movable for contact at independent selected portions of the user's head 12. Further, each extension finger 16, 16' is operably coupled to the respective vibrating device 14, 14' for the transmission of the vibrating action thereof to its tip portion 17, 17'. Accordingly, the massager apparatus 10 of the present invention provides a facial massage formed for stationary mounting to a user's head, via headset assembly 11, which includes at least one (but preferably two) elongated, bendable and retainable extension finger 16 which enables vibration transmission of the vibration action to tip portion 17 thereof. Through manual manipulation and retainment of the position of extension finger 16, most regions of the face can be reached for direct massaging contact with the vibrating tip portion.

Headset assembly 11 is preferably U-shaped having two generally flat or planar leg portions 20, 20' depending downwardly from a top portion thereof. Leg portions 20, 20' are formed to straddle the opposing sides of the user's head for comfortable mounting and support of the headset assembly to the head. Headset assembly 11 is preferably composed of a semi-flexible high impact plastic for strength and durability and lightweight.

Headset assembly 11 preferably houses controller device 15 at the top portion thereof. Controller device 15, the operation of which is to be discussed in greater detail below, includes the power source, i.e., a battery, and circuitry to control the vibration amplitude/frequency and On/Off control of vibration devices 14, 14' through at least two control knobs 21, 21'.

Figure 3:
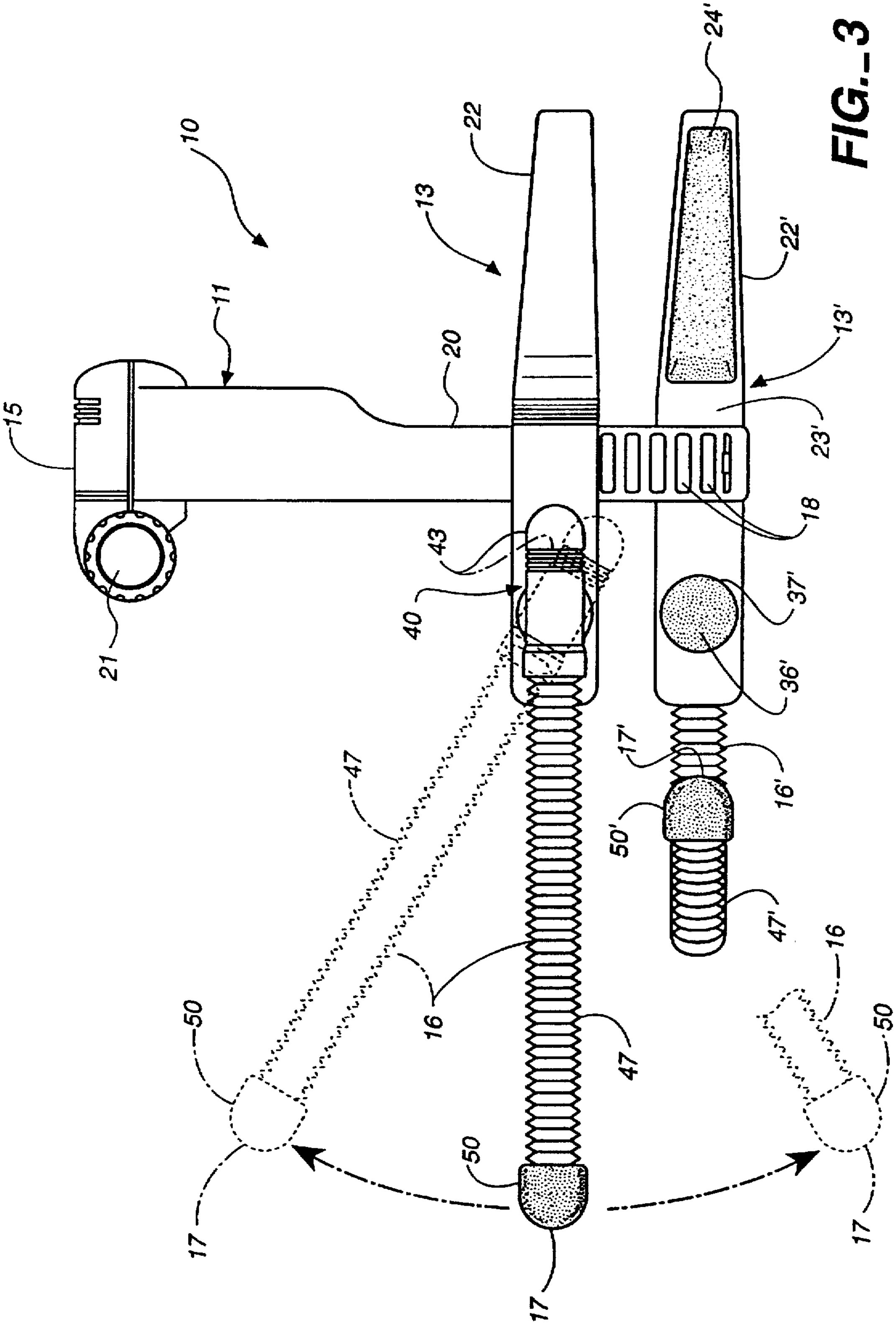
FIG. 3 is a side elevation view of the head mounted facial massager apparatus of FIG. 1, and illustrating pivotal displacement of the extension fingers.

Turning now to FIGS. 1–3, it can be shown that the individual vibration generating assemblies 13, 13' of the present invention are preferably identical mirror-images of one another. Hence, for the ease of description, only one vibration generating assembly 13 will be described in detail.

The vibration generating assembly includes a hollow motor housing 22,22' formed to carry and support vibration device 14 therein. Motor housing 22,22' is preferably elongated and is oriented generally perpendicular to leg portion 20. FIG. 2 illustrates that a rear or tail portion of motor housing 22 is curved inwardly to conform to the user's head for support thereof. An inner wall 23 of the tail portion includes a foam back cushion 24 formed to seat against the back of the user's head. This arrangement enables the massager apparatus 10 to be worn in a comfortable, supportive manner while a massage is being given.

Motor housing 22 provides a receiving slot 25 (FIG. 4) formed and dimensioned for sliding receipt of a transverse cross-sectional dimension of leg portion therethrough. Hence, motor housing 22 can be selectively height-adjusted longitudinally along leg portion 20 for movement thereof relative the user's head. Leg portion 20 includes a plurality of spaced-apart ribs 18 which frictionally support and engage the wall of receiving slot 25 to releasably retain motor housing 22 against leg portion 20. Finally, similar to the headset assembly, motor housing 22 is preferably composed of a semi-flexible high impact plastic.

Figure 4:
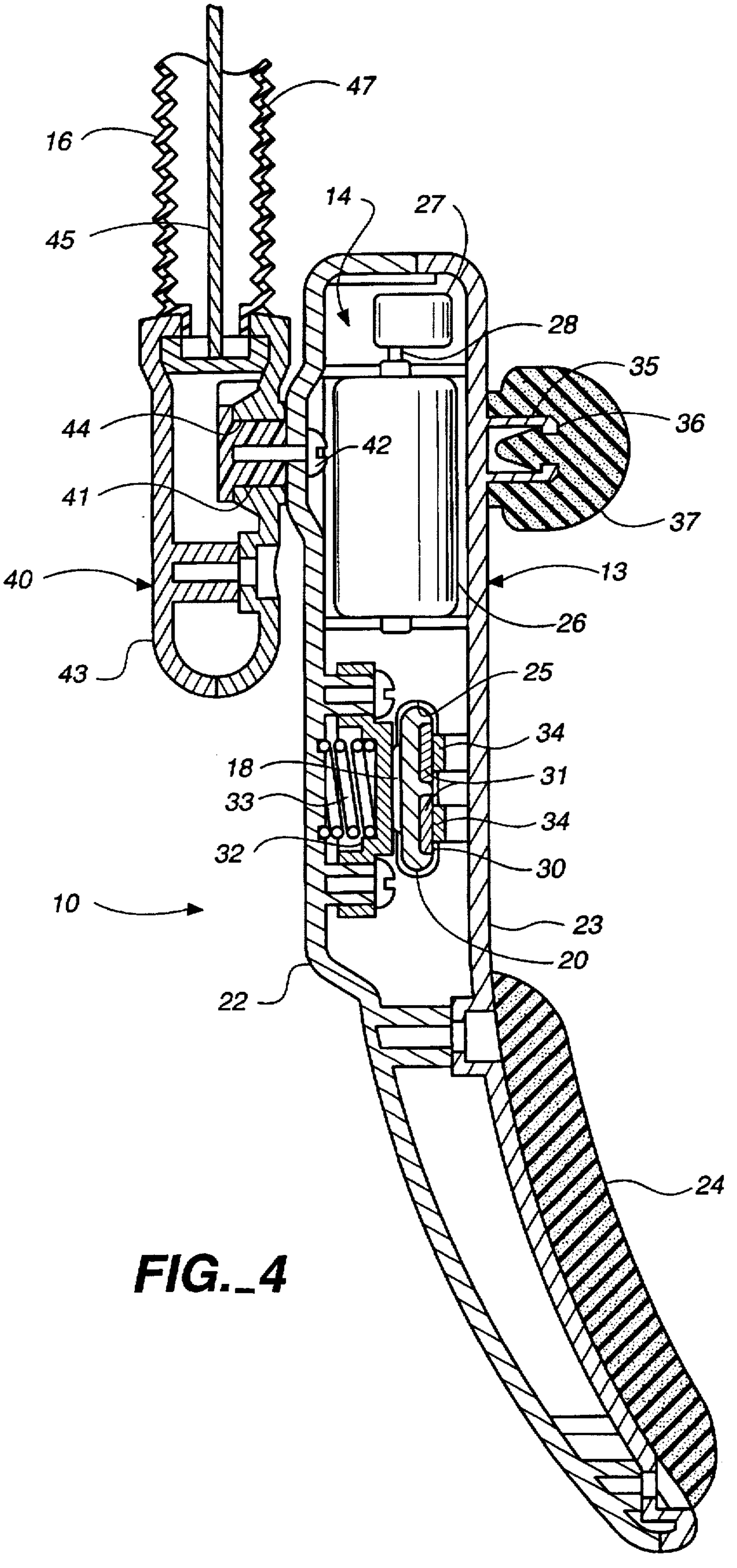
FIG. 4 is an enlarged, top plan view, in cross-section, of the head mounted facial massager apparatus of FIG. 1.

As shown in FIG. 4, vibration device 14 is preferably provided by an electronic motor assembly 26 rotatably supporting an eccentric weight 27 which generates the vibration action upon rotation about output shaft 28. Through rigid mounting of motor assembly 26 to motor housing 22, vibration action can be efficiently transmitted throughout the motor housing due to the housing rigidity. Briefly, to transmit signals from controller device 15 to vibration device 14, an interior wall 30 of leg portion 20 includes embedded contact strips 31 (FIGURES 1 and 4) extending longitudinally therealong. Positioned proximate receiving slot 25 is a movable spring plate 32 biased into sliding contact with leg portion 20, by compression spring 33, which causes contact strips 31 to electrically communicate with and contact motor contacts 34 (FIG. 4). Accordingly, through manual operation of knobs 21, 21' of controller device 15, the common frequency and duty cycle of power level of each motor assembly 26 can be user controlled.

Further, extending outwardly from the inner wall 23 of motor housing 22, proximate motor assembly 26, is a temple post 35 having a nub portion 36 at a distal end thereof. Temple post 35 is generally rigid and preferably strategically positioned such that nub portion 36 contacts the temple of said user's head for massage thereof. Manual positioning of motor housing 22 longitudinally along leg portion 20, hence, enables height-adjustment of temple post 35 relative the user's temple.

Upon operation of motor assembly 26, vibration action generated by the motor assembly is transmitted to the nub portion which focuses the vibration action on the user's temple for more direct massage thereof. A foam temple cushion 37 is preferably included, which covers nub portion 36, for additional comfort.

In the preferred form, vibration generating assembly 13 further includes extension finger 16 mounted to and extending forwardly of motor housing 22. FIGS. 3 and 4 illustrate that extension finger 16 is preferably pivotally mounted to housing 22 through a swivel joint 40 situated at a position opposite temple post 35. Swivel joint 40 includes a bearing ring 41 rigidly mounted to motor housing 22 through screw 42, and a base member 43 providing an aperture 44 formed and dimension for pivotal receipt of bearing ring 41 therein. Accordingly, as shown in phantom lines in FIG. 3, extension finger 16 can be pivotally displaced about a generally horizontal axis for displacement of tip portion 17 of extension finger 16 above and below motor housing 22.

Extension finger 16 preferably includes an elongated, metal bending strip 45 having one end fixedly mounted to swivel joint 40, and an opposite end mounted to tip portion 17. Bending strip 45 is provided by a material sufficiently malleable for manual manipulation to reposition and retain tip portion 17, as indicated by arrow 46 in FIG. 2, about the user's face for contact therewith. It will be understood, however, that bending strip 45 must also be sufficiently rigid to enable transmission of the vibration action to tip portion 17. Accordingly, the path of transmission of the vibration action generated by motor assembly 26 is through motor housing 22, swivel joint 40, bending strip 45 and onto tip portion 17.

A flexible bellow tube or the like encloses bending strip 45 therein for protection and shielding of the bending strip. Bellow tube 47 is preferably composed of lightweight plastic tubing. Finally, a foam face cushion 50 is included, which covers tip portion 17, for additional comfort thereof.

Figure 5A:
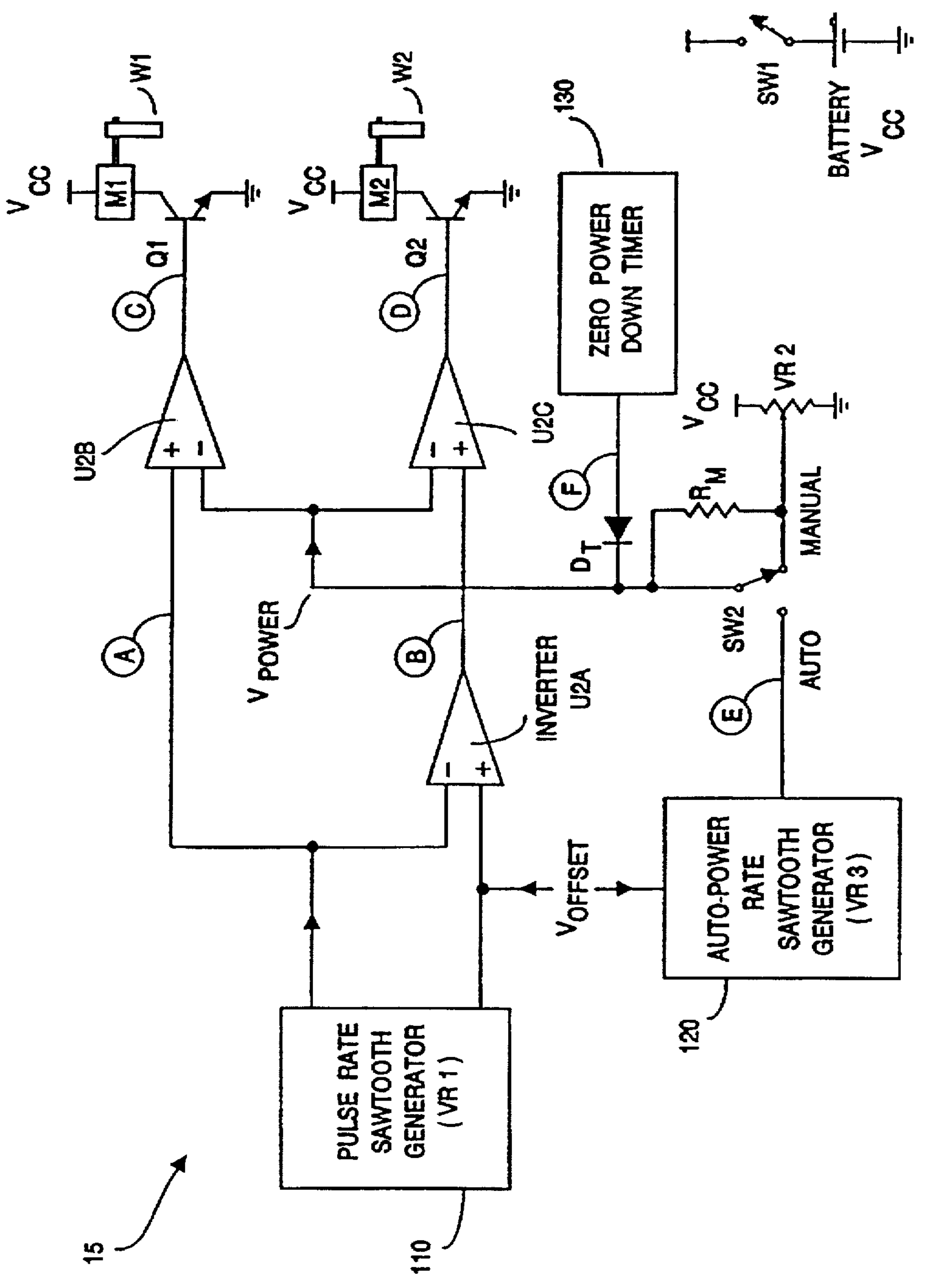
FIG. 5A is a block diagram of an electronic controller, according to the present invention.

FIG. 5A depicts the general operation of controller 15. Controller 15 includes a pulse rate sawtooth generator 110, that permits user-variation of the operating frequency of motor assemblies 26, which are depicted in FIG. 5A as M1 (motor 1) and M2 (motor 2). FIG. 5A also depicts the eccentric weights, shown here as W1 and W2, attached to the shafts of motors M1 and M2 respectively. A potentiometer VR1 connected to knob 21 allows the user to vary the repetition rate of the motor drive signal pulse train from about 1 Hz to about 10 Hz.

As will be described, rotation of the motor shafts (and thus the weights, e.g., W1, W2) is a function of the repetition rate and of the duty cycle of the motor drive signal pulses.

Figure 5B:
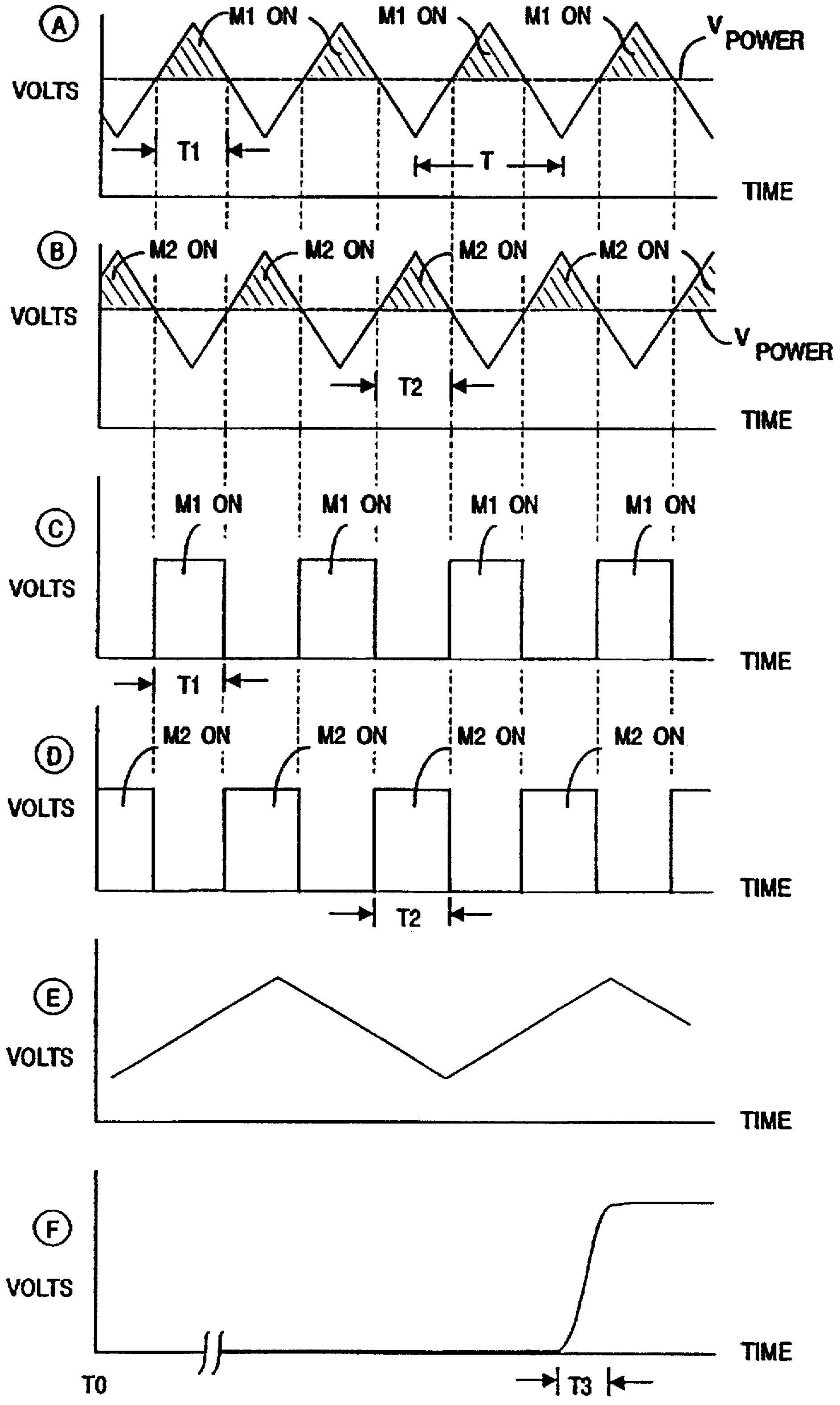
FIG. 5B depicts waveforms present at different regions of the electronic controller shown in FIG. 5A for a duty cycle of 50%.

As shown in FIG. 5B, waveform A, the output of module 110, is a sawtooth voltage whose period T is varied by VR1 preferably from about 0.1 second to about 1 second. This waveform has a DC offset, noted as $V_{OFFSET}$ that is a fraction of the operating $V_{cc}$ Potential. Because FIG. 5B depicts a 50% duty cycle condition, the DC level noted as $V_{POWER}$ coincides with the DC level that is $V_{OFFSET}$. An inverter U2A causes waveform B to have the same DC offset, but to be inverted relative to waveform A. A typically 9 V battery that is connected to the remainder of controller 15 through an ON/OFF switch SW1 provides $V_{cc}$ to the controller and motors M1 and M2. If desired, SW1 may be ganged with potentiometer VR1.

Waveforms A and B are coupled to the non-inverting input of operational amplifiers U2B, U2C respectively. A threshold voltage, denoted $V_{POWER}$, is coupled to the inverting input of each of these two operational amplifiers. When mode switch SW2 is in the MANUAL power change mode, a potentiometer VR2, coupled to knob 21', permits the user to manually vary the duty cycle, or power level, of the two motors. As VR2 is varied, the magnitude of $V_{POWER}$ in waveform A in FIG. 5B changes. (The role of switch SW2 will be described following.) The action of operational amplifiers U2B and U2C is such that motor Ml is energized whenever waveform A exceeds the magnitude of $V_{POWER}$, and motor M2 is energized whenever waveform B exceeds the magnitude of $V_{POWER}$. For ease of understanding, the regions of waveforms A and B are cross-hatched in FIG. 5B. As will be described shortly with respect to FIGS. 5C and 5D, if the $V_{POWER}$ voltage level is increased, the duty cycle is decreased, and vice versa. In FIG. 5B, VR2 has been adjusted to make the magnitude of $V_{POWER}$ a DC level that results in a 50% duty cycle. Thus, M1 will be energized for a time T1 equal to 50% of T, then Ml will be de-energized at the same moment that M2 will be energized for a time T2 equal to 50% of T, then M2 will be de-energized at the same moment that M1 will be energized, and so on.

Waveforms C and D depict the respective outputs of operational amplifiers U2B and U2C, and thus the input waveforms to motor drive transistors Q1 and Q1.

Thus, for a time T1 waveform A exceeds the $V_{POWER}$ threshold level, and waveform C turns on transistor Q1, which causes motor M1 to be energized. Waveform A then falls below the $V_{POWER}$ threshold level and waveform C causes transistor Q1 to turn off, which de-energizes motor M1. Because duty cycle is 50% in FIG. 5B, precisely when A falls below the $V_{POWER}$ threshold, waveform B will exceed the $V_{POWER}$ threshold, and waveform D turns on transistor Q2, which causes motor M2 to be energized for a time T2. When waveform B falls below the $V_{POWER}$ threshold, waveform D turns off transistor Q2, which de-energizes motor M2, and so on. In FIG. 5B, because $V_{POWER}$ is set at a DC level representing a 50% duty cycle, T1=T2=0.5T.

Figure 5C:
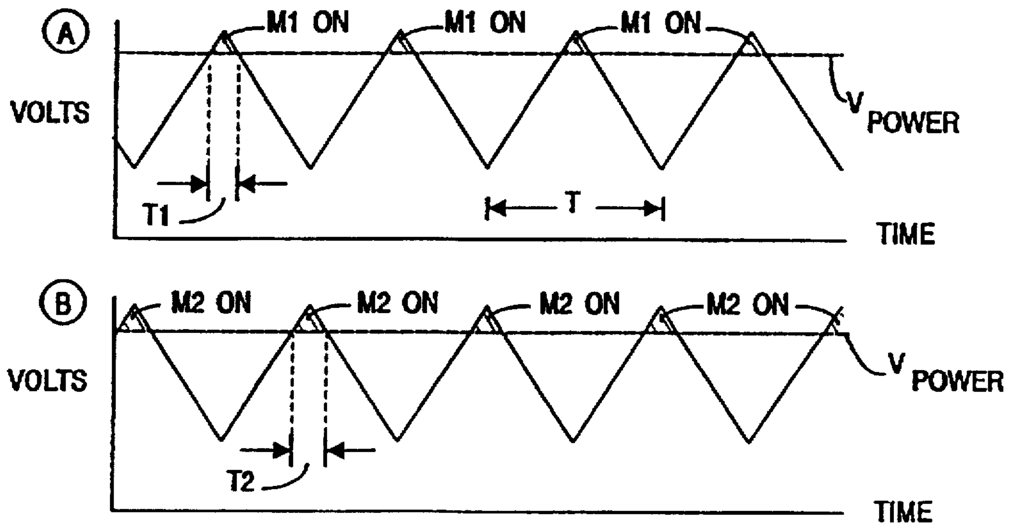
FIG. 5C depicts sawtooth waveforms for a duty cycle of about 10% for the electronic controller shown in FIG. 5A.

FIG. 5C depicts the case where the user has adjusted VR2 upward, towards $V_{cc}$, to increase the voltage threshold level $V_{POWER}$. Waveform A now exceeds the $V_{POWER}$ threshold for only a small fraction of the waveform period T, e.g., T1<<T, and similarly waveform B now exceeds the $V_{POWER}$ threshold for only a brief time T2, e.g., T2<<T. The duty cycle is thus reduced, with FIG. 5C depicting a duty cycle of about 10%.

One advantage of reduced duty cycle is that less current is drawn from the battery providing $V_{cc}$, thus increasing battery lifetime. Although duty cycle is reduced, the use of two motors sequentially energized, as shown, still provides a pleasant and effective vibrating massage.

Figure 5D:
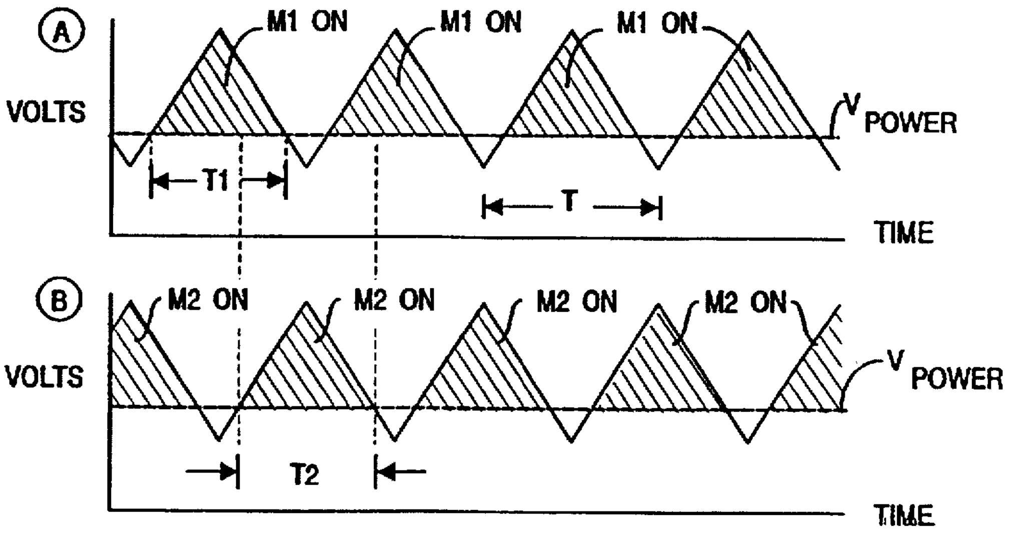
FIG. 5D depicts sawtooth waveforms for a duty cycle of about 90% for the electronic controller shown in FIG. 5A.

FIG. 5D depicts the case where VR2 has been used-adjusted to decrease the magnitude of the $V_{POWER}$ threshold. Waveform A and waveform B each now exceed the threshold for nearly all of period T, e.g., T1≈T, T2≈T, with the result that motors M1 and M2 are on nearly all of the time. The VPO.R threshold level depicted in FIG. 5D represents a perhaps 90% duty cycle. It is seen from FIG. 5D that when the duty cycle exceeds 50%, the start of the time T2 will overlap the end of the time T1, such that both motors M1 and M2 are simultaneously energized during the overlap time.

The user's ability to manually vary the repetition rate of the waveform A/B sawtooth with potentiometer VR1, and to independently vary motor duty cycle with potentiometer VR2 allows the present invention to provide patterns of vibration that have a wide dynamic range. This is in stark contrast to prior art devices that have a fixed repetition rate, a fixed duty cycle, and an essentially static pattern of vibration.

To provide still greater flexibility, the present invention optionally includes an auto-power rate sawtooth generator module 120. As will be described with reference to FIG. 6, module 120 is analogous to module 110. As shown by waveform E in FIG. 5B, module 120 outputs a slowly changing sawtooth voltage. Waveform E has a period that may be user con-trolled by a potentiometer VR3 to vary from perhaps 10 seconds to one minute. Switch SW2 may be mechanically ganged with VR3. (The adjustment knob for VR3 is not shown in FIG. 1.)

In the AUTOMATIC power mode, switch SW2 is switched away from VR2 and onto the sawtooth output of module 12. The presence of resistor $R_M$ causes the VR2-set level of $V_{POWER}$ to now be augmented with a slowly changing sawtooth waveform. The result is a continuously varying duty cycle in motors M1 and M2.

The AUTOMATIC power mode of operation will be appreciated by examining FIGS. 5C and 5D and imagining that the $V_{POWER}$ threshold level slowly and automatically increases and decreases over a period lasting from a few seconds to perhaps longer than a minute. As the magnitude of the $V_{POWER}$ waveform E rises the duty cycle decreases (e.g., FIG. 5C), and as the waveform E magnitude falls, the duty cycle increases (e.g., FIG. 5D).

In the AUTOMATIC power mode, the strength of the massage provided by the present invention will slowly vary, producing a dynamically changing massage sensation. The presence of resistor $R_m$ enables waveform E to augment the DC voltage produced by potentiometer VR2. Preferably the peak-to-peak voltage of waveform E represents about 30% of the maximum $V_{POWER}$ level that may be manually provided by changing VR2. This range provides a relaxing dynamic range of automatically changing duty cycle, and thus slowly varying strength of the massage produced by motors M1 and M2. As shown by FIG. 5A, controller 15 may also include a zero power down timer module 130. When $V_{cc}$ is first connected to the controller, e.g., by closing switch SW1, time module 130 is energized, e.g., see time TO, FIG. 5B. Module 130 performs a one-shot function and after a preset time period of perhaps ten minutes, e.g., from time To to onset of time T3 in waveform F, module 130 outputs a positive-going pulse. The risetime of this pulse is intentionally slowed for a time T3 with a resistor and capacitor, as shown in waveform F. After perhaps $T3 \approx 30$ seconds, the magnitude of waveform F will exceed the level of $V_{POWER}$, forward biasing diode $D_T$.

As the magnitude of waveform F continues to rise, the duty cycle of the motors decreases, as is apparent by comparing FIG. 5D with FIG. 5C. Finally, when waveform F is more positive than the $V_{POWER}$ voltage level representing 0% duty cycle, the duty cycle of motors M1 and M2 is zero. This 0% duty cycle $V_{POWER}$ level is a voltage higher than the most positive peak of waveform A or waveform B (see for example FIG. 5C, wherein $V_{POWER}$ would be made still more positive). Of course, a zero power down timer function could be implemented in other ways as well.

Figure 6:
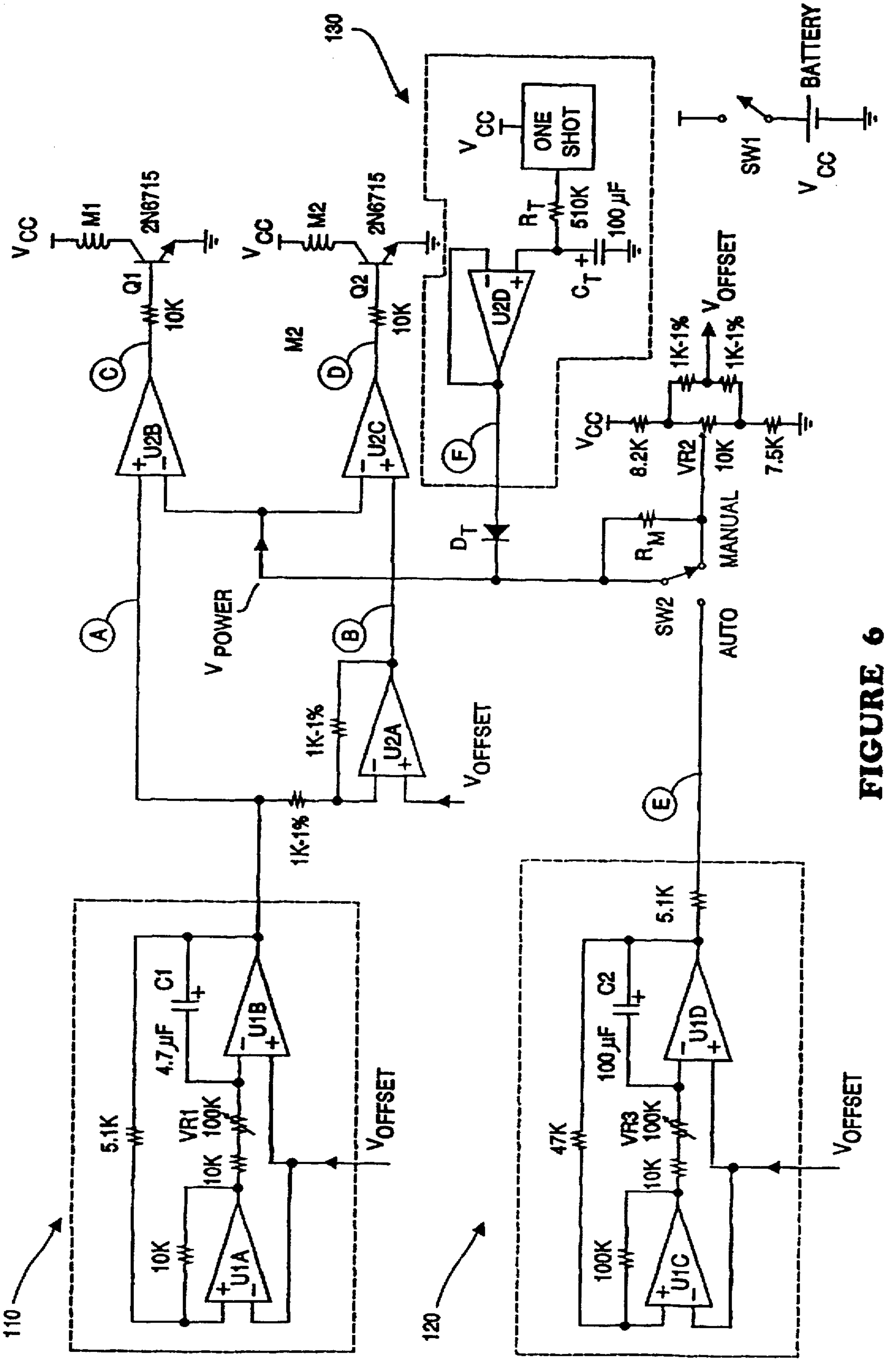
FIG. 6 is a schematic of a preferred embodiment of an electronic controller, according to the present invention.

FIG. 6 is a schematic of a preferred embodiment of controller 15. The pulse rate sawtooth generator 110 is implemented using operational amplifiers U1A and U1B. These and the other operational amplifiers shown in FIG. 6 preferably are quad integrated circuit devices, e.g., LM 324, LMC 6484, LMC 660, LMC 6034, among others. A square wave output voltage from U1A is dropped across VR1 and its series resistance to produce a square wave current that U1B integrates. In response, U1B generates a voltage ramp across low leakage capacitor C1. This ramp appears the output pin of U1B and has a polarity that is opposite to the voltage appearing at the output of U1A.

A resistor-divided fraction of the ramp signal is feed back to U1A, reversing the polarity of the U1B output, which causes the ramp at the output of U1B to reverse polarity. As a result, generator 110 provides at the output pin of U1B a sawtooth waveform A having a peak-to-peak magnitude of a volt or two, and having a period T that is proportional to VR1 and C1.

In the preferred embodiment, VR1 permits the user to vary the period T from about 0.1 second to about 1 second, although other periods could of course be provided. If desired, light emitting diodes ("LED"s) may be coupled between the output of U1B and ground to provide the user with a visual indication of the repetition rate of waveform A (and thus also waveform B).

As shown in waveform A in FIGS. 5B–5D, the sawtooth waveform has a DC offset that is resistor-divided from $V_{CC}$ to be perhaps 50% $V_{cc}$. To stabilize this $V_{OFFSET}$ , 1% resistors are used in the resistor divider (where shown in FIG. 6), and zener voltage regulation preferably is provided to the integrated circuits implementing the pulse rate sawtooth generator. If desired, controller 15 may also include a voltage regulator integrated circuit that regulates the DC voltage from the battery (BATTERY) powering the controller circuit to provide a more constant $V_{cc}$ voltage to the controller circuitry.

As was indicated by FIG. 5A, the non-inverting input of operational amplifier U2A is coupled to the $V_{OFFSET}$ voltage. The inverting input of U2A is coupled to the sawtooth waveform A, available from the output of U1B. U2A is configured as a unity gain voltage follower and outputs waveform B (e.g., as shown in FIG. 5B). As such, waveform B is an inverted sawtooth waveform having the same polarity $V_{OFFSET}$ as the waveform A signal at the output of U1B.

Sawtooth waveforms A and B are coupled to the non-inverting inputs of operational amplifiers U2B and U2C respectively. The inverting inputs of these amplifiers are coupled to the $V_{POWER}$ voltage described above, and depicted in the Figures, e.g., waveforms A and B in FIG. 5B.

If AUTO/MANUAL switch SW2 is in the MANUAL position, then the user-controlled potentiometer VR2 will adjust $V_{POWER}$ to a DC level that is a fraction of $V_{cc}$. On the other hand, if SW2 is set to the AUTO position, the $V_{POWER}$ will be a slowly changing sawtooth signal. This signal results from the output of the auto-power rate sawtooth generator 120 augmenting (due to the presence of resistor $R_M$) the DC output set by potentiometer VR2. Generator 120 is somewhat similar to the pulse-rate sawtooth generator 110, and includes operational amplifiers U1C, U1D, a low leakage integrating capacitor C2, VR3 and associated resistors.

Similarly to what was described with respect to generation of waveform A, operational amplifiers U1C and U1D generate sawtooth waveform E (see FIG. 5B). In the preferred embodiment, waveform E has a period that may be varied with potentiometer VR3 from about a second to a minute or more. Obviously the length of this period may be increased or decreased by increasing or decreasing the value of low leakage capacitor C2, and/or VR3 and its series resistor.

Regardless of whether the $V_{POWER}$ voltage level was generated manually using potentiometer VR2, or automatically by generator 120, it is appreciated that the level of $V_{POWER}$ determines the duty cycle of motors M1 and M2. Waveforms A and B as well as the $V_{POWER}$ voltage are input to high gain operational amplifiers U2B and U2C, whose respective outputs are waveforms C and D (see FIG. 5B). Because these amplifiers are run at high gain, waveforms C and D will be pulse trains, whose duty cycle is determined by the magnitude of the $V_{POWER}$ level, as was described herein.

Waveforms C and D are coupled to the base leads of motor driver transistors Q1 and Q2 respectively. In the preferred embodiment, motors M1 and M2 are each DC motors that require perhaps 40 mA to perhaps 300 mA, and Q1 and Q2 preferably are 2N6715 or equivalent devices.

When pulse train waveform C or D is high, the respective transistor Q1 or Q2 turns on hard, bringing the collector lead essentially to ground potential. This causes $V_{cc}$ to pass through the winding of the respective motor M1 or M2, energizing the motor. Although not shown in FIG. 6, a diode and capacitor preferably are coupled in shunt across each motor winding to minimize transient voltages that could damage the motor driver transistors Q1 and Q2. The zero power down timer 130 preferably is implemented with a 4060 timer integrated circuit that is configured to perform a one-shot function. The one-hot is activated when switch SW1 applies DC operating voltage from the battery (BATTERY) to the integrated circuits and motor windings shown in FIG. 6.

The one-shot output is low (e.g., about 0 VDC) for a predetermined period of perhaps 10 minutes following $V_{CC}$ power-on to controller 15. After that period, the one-shot output rises to approximately $V_{cc}$. The risetime of this positive-going pulse is intentionally slowed with resistor RT and capacitor $C_T$. The slowed pulse is then passed through a voltage follower U3C, whose output, waveform F, is coupled through diode $D_T$ to the $V_{POWER}$, inverting inputs of U2B and U2C.

Until such time as the voltage level of waveform F on the anode side of diode $D_T$ exceeds whatever the level of $V_{POWER}$ on the cathode side happens to be, the timer circuitry 130 does not affect operation of the motors M1 and M2. However, perhaps eleven minutes after switch SW1 powers-on controller 15, waveform F will slowly increase to a level that forward biases $D_T$ regardless of how positive the magnitude of $V_{POWER}$ might be. When $D_T$ is forward biased, the magnitude of $V_{POWER}$ seen by the inverting inputs of amplifiers U2B and U2C will increase as waveform F increases.

As best seen from FIG. 5C, once this magnitude of $V_{POWER}$ increases sufficiently to exceed the uppermost magnitude of waveform A (or waveform B), motor duty cycle drops to 0%. Since the maximum magnitude of waveform A and waveform B will be less than $V_{CC}$, and waveform F can essentially reach $V_{CC}$, eventually a zero duty cycle condition is guaranteed. In stark contrast to power-down in prior art massage devices, the duty cycle in the present invention will gradually be reduced to zero, a preset period after power-on. The length of the gradual reduction is a function of the magnitude of RT, and CT, and preferably is at least thirty seconds. Of course the length of the preset period may be changed to other than about ten minutes, and $R_T$ and/or $C_T$ may be changed to produce a gradual reduction lasting other than about thirty seconds.

A user wearing the present invention could, for example, fall comfortably asleep while being massaged. After the preset period of time, the zero duty cycle is gradually arrived at. In contrast to the prior art, there is no abrupt transition from full massage to no massage (e.g., zero duty cycle). If desired, the zero duty cycle condition could also be used to electronically disconnect the battery from controller 15, to further reduce the current drawn by controller 15 in a zero duty cycle condition.

Those skilled in the art of circuit design will appreciate that many variations can be made to the disclosed controller. For example, the preferred embodiment inverts waveform A to produce waveform B, and impresses a common $V_{OFFSET}$ voltage on each waveform. Alternatively, one could generate a waveform B that was in phase with waveform A, but had an inverted polarity $V_{OFFSET}$ voltage. Duty cycle would still be varied by varying the level of the $V_{POWER}$ voltage.

Modifications and variations may be made to the disclosed embodiments without departing from the subject and spirit of the invention as defined by the following claims. For example, controller 15 may be used to control the duty cycle and repetition rate of motors used in other than a head mounted massage unit.

What is claimed is:

1. A controller that controls first and second electric motors in a vibrating apparatus, the first motor operating in response to a first motor drive signal generated by said controller, and the second motor operating in response to a second motor drive signal generated by said controller, said controller comprising:

a pulse rate generator providing a periodic signal having a repetition rate at which said electric motors are to be pulsed by the motor drive signals;

means for providing a voltage, $V_{POWER}$, proportional to a desired operating duty cycle of said electric motors; and means for comparing said periodic signal with said $V_{POWER}$ voltage and for providing first and second motor drive signals whose duty cycle is said desired operating duty cycle and is proportional to a voltage difference between said periodic signal and said $V_{POWER}$ voltage.

2. The controller of claim 1, wherein when duty cycle exceeds 50% the first and second motor drive signals at least partially overlap in time but do not overlap for duty cycle less than 50%.

3. The controller of claim 1, wherein:

said pulse rate generator provides complementary first and second periodic signals that each have a common DC voltage offset; and said means for comparing and for providing includes:

a first comparator, coupled to receive the first periodic signal and said $V_{POWER}$ voltage, outputting the first motor drive signal in response to a magnitude difference therebetween;

a second comparator, coupled to receive the second periodic signal and said $V_{POWER}$ voltage, outputting the second motor drive signal in response to a magnitude difference therebetween;

wherein a variation in said $V_{POWER}$ voltage varies duty cycle of the electric motors causing variation in intensity of vibrations produced by said apparatus.

4. The controller of claim 1, wherein:

said means for providing a voltage includes a circuit generating a time varying $V_{POWER}$ waveform;

wherein duty cycle of said first and second electric motors vary continuously.

5. The controller of claim 4, wherein said controller is user switchably-operable between a manual mode wherein said $V_{POWER}$ voltage is manually adjustable, and an automatic mode wherein said $V_{POWER}$ voltage is a continuously varying pattern.

6. The controller of claim 1, further including a timer to gradually force said $V_{POWER}$ voltage to a magnitude causing zero duty cycle a preset time from application of operating power to said facial massager apparatus.

7. The controller of claim 1, wherein said pulse rate generator provides a periodic sawtooth waveform.

8. The controller of claim 3, wherein said time varying $V_{POWER}$ waveform describes a periodic sawtooth waveform.

9. The controller of claim 1, wherein:

said means for providing a voltage includes a circuit generating a time varying $V_{POWER}$ waveform; and further including:

a timer that gradually forces said $V_{POWER}$ voltage to a magnitude causing zero duty cycle a preset time from application of operating power to said facial massager apparatus;

wherein during said preset time duty cycle of said first and second electric motors can vary continuously, but after said preset time duty cycle is gradually forced to zero.

10. The controller of claim 8, wherein said controller is user switchably-operable between a manual mode wherein said $V_{POWER}$ voltage is manually adjustable, and an automatic mode wherein said $V_{POWER}$ voltage is a continuously varying pattern.

11. The controller of claim 1, wherein said pulse rate generator provides a periodic sawtooth waveform.

12. The controller of claim 1, wherein said controller, said first and second electric motors, and said vibrating apparatus are all mounted on a headset sized to be worn on a user's head.

* * * * *

UNITED STATES PATENT AND TRADEMARK OFFICE

CERTIFICATE OF CORRECTION

PATENT NO. : 5,767,634

DATED : June 16, 1998

INVENTOR(S) : TAYLOR et al.

It is certified that error appears in the above-identified patent and that said Letters Patent is hereby corrected as shown below:

Column 3, line 38, delete "13,13-" and insert therefore --13, 13'--.

Column 3, line 40, delete "16, 16-" and insert therefore --16, 16'--.

Column 4, line 39, immediately preceding "Briefly" insert a new paragraph.

Column 5, line 67, immediately following "following.)" and preceding "The" insert a new paragraph.

Column 6, line 16, immediately following "Q1." delete the new paragraphing as lines 16-17 are part of the same paragraph.

Column 6, line 50, delete "VPO,R" and insert therefore --$V_{POWER}$--.

Column 7, line 36, delete "To" and insert therefore --TO--.

Column 9, line 13, immediately following "Q2." and preceding "The zero" insert a new paragraph.

Column 9, line 46, immediately following "guaranteed." and preceding "In stark" insert a new paragraph.

UNITED STATES PATENT AND TRADEMARK OFFICE

CERTIFICATE OF CORRECTION

PATENT NO. : 5,767,634

DATED : June 16, 1998

INVENTOR(S) : TAYLOR et al.

It is certified that error appears in the above-identified patent and that said Letters Patent is hereby corrected as shown below:

Claim 10, column 12, delete "claim 8" and insert therefore --claim 9--.

Signed and Sealed this

Twenty-ninth Day of September, 1998

Attest:

BRUCE LEHMAN

*Attesting Officer* *Commissioner of Patents and Trademarks*